United States Patent [19]

Sholder

[11] Patent Number: 4,817,605
[45] Date of Patent: Apr. 4, 1989

[54] PACEMAKER SYSTEM AND METHOD FOR MEASURING AND MONITORING CARDIAC ACTIVITY AND FOR DETERMINING AND MAINTAINING CAPTURE

[75] Inventor: Jason A. Sholder, Canoga Park, Calif.

[73] Assignee: Siemens-Pacesetter, Inc., Sylmar, Calif.

[21] Appl. No.: 27,715

[22] Filed: Mar. 19, 1987

Related U.S. Application Data

[62] Division of Ser. No. 662,723, Oct. 19, 1984, Pat. No. 4,686,988.

[51] Int. Cl.$^4$ .............................................. A61N 1/36
[52] U.S. Cl. ............................................... 128/419 PT
[58] Field of Search ................... 128/419 PG, 419 PT

[56] References Cited

U.S. PATENT DOCUMENTS

| | | | |
|---|---|---|---|
| 3,618,615 | 11/1971 | Greatbatch | 128/419 PG |
| 3,651,799 | 3/1972 | Daynard | 128/419 PT |
| 3,759,265 | 9/1973 | Thaler et al. | 128/419 PG |
| 3,782,367 | 1/1974 | Hochberg et al. | 128/419 PT |
| 3,949,758 | 4/1976 | Jirak | 128/419 PT |
| 4,543,963 | 10/1985 | Gessman | 128/419 PG |
| 4,674,509 | 6/1987 | DeCote, Jr. | 128/419 PT |

*Primary Examiner*—William E. Kamm
*Attorney, Agent, or Firm*—Bryant R. Gold; Leslie S. Miller

[57] ABSTRACT

A system for determining P-wave or R-wave capture in response to pacemaker supplied electrical stimuli. One embodiment includes a conventional bipolar atrial lead having a tip electrode, connected to an atrial pulse generator circuit within an implantable pacemaker, and a ring electrode, spaced apart from the tip electrode, connected to a P-wave sensing EGM amplifier within the pacemaker. The bandpass characteristics of the P-wave sensing EGM amplifier allow detection of all electrical frequencies in the atrium within the bandpass chosen. The output signal from this amplifier is selectively telemetered to an external receiver, as is a signal indicating the generation of an atrial stimulation pulse, where the occurrence of atrial stimulation pulses and P-waves can be monitored. In operation, if constant time intervals between the monitored atrial stimulation pulses and P-wave occurrences are present, P-wave capture has occurred. In the event of variable time intervals, capture has not occurred and the magnitude of the atrial stimulation pulses can be increased until P-wave capture does occur. An alternative embodiment measures this time differential and makes the stimulation pulse adjustment automatically. Other embodiments use the same manual or automatic systems to determin R-wave capture.

12 Claims, 5 Drawing Sheets

PACEMAKER SYSTEM AND METHOD FOR MEASURING AND MONITORING CARDIAC ACTIVITY AND FOR DETERMINING AND MAINTAINING CAPTURE

This is a divisional of co-pending application Ser. No. 662,723 filed on 10/19/84 now issued as U.S. Pat. No. 4,686,988.

TECHNICAL FIELD

The invention relates to implantable heart pacemakers, and more specifically to heart pacemakers having a capability to stimulate the atrium and sense the atrial response.

BACKGROUND ART

"Capture" is defined as a cardiac response to a pacemaker stimulation pulse. When a pacemaker stimulation pulse stimulates either the heart atrium or the heart ventricle during an appropriate portion of a cardiac cycle, it is desirable to have the heart respond to the stimulus provided Every patient has a threshold which is generally defined as a minimum amount of stimulation energy required to effect capture. It is usually desired to achieve capture at the lowest possible energy setting yet provide enough of a safety margin so that should the patient's threshold increase, the output of an implanted pacemaker would be sufficient to maintain capture.

Capture is usually assessed by means of an electrocardiogram (ECG) measured through ECG electrodes placed on the patient's limbs and/or chest. When a patient is connected to a typical ECG monitor and the pacemaker is providing stimulation pulses, the physician monitors the output to assess whether each pacing pulse, which is seen as a spike, is followed by a cardiac response. Ventricular capture is relatively easy to assess in that each ventricular stimulation produces a very large R-wave. Determination of atrial capture in response to an atrial stimulation pulse is a more difficult task. Atrial capture in response to stimulation pulses has been viewed on an electrocardiogram as P-waves following each atrial stimulation by a constant time interval. One prior art embodiment utilized dual sensing electrodes and suggests the heart action is 15 to 20 milliseconds after the stimulus. (See Goldreyer, U.S. Pat. No. 4,365,639.) However, the time delay varies considerably depending on the patient, administered drugs, electrolyte balance, proximity of sensing electrode to stimulating electrode and other factors. Further, it is almost impossible to guarantee that a P-wave will be of a sufficient amplitude to be seen on a standard ECG scan. In order to verify atrial capture in patients with intact cardiac conduction, the physician must pace atrially and observe ventricular response to the paced atrial rate. However in patients with heart block, the physician may not be able to determine atrial capture because of the lack of conduction from the atrium to the ventricle, thus preventing the ventricle from responding to atrial stimulation pulses. In such cases the physician may have to rely on fluoroscope evaluation of cardiac wall motion in response to the atrial stimulation to ascertain atrial or P-wave capture.

Another method for determining atrial capture is to transmit the signal appearing on the atrial stimulation electrode to an external viewing device. Some of the newer pacemakers have the capability to transmit electrogram (EGM) signals appearing at either the atrial electrode or the ventricular electrode in real time to an external monitoring device for real-time evaluation by a physician. (See, for example, U.S. Pat. No. 4,232,679 to Schulman.) However, due to the large magnitude of a stimulation pulse with respect to the P-wave signal, and the closeness in time between the stimulation pulse and the occurrence of the P-wave, the atrial sensing amplifiers of conventional pacemakers saturate in the presence of a stimulation pulse and mask the P-wave. Thus as a practical matter, utilization of EGM signals appearing at the stimulation electrode is not effective for determining if P-wave capture has occurred. One feature of the present invention solves this problem by providing an apparatus for determining P-wave capture through use of a conventional implantable bipolar atrial electrode without having to utilize the stimulation electrode for P-wave detection.

DISCLOSURE OF INVENTION

The invention provides a system useful for determining P-wave capture in response to pacemaker supplied atrial electrical stimuli. The system includes a first lead means having at its distal end a first exposed electrically conductive electrode and a second exposed electrically conductive electrode spaced apart from the first electrode a distance no greater than that required for the first and second electrodes to be operably located within a user's heart atrium. The first electrode is electrically connected to a first terminal means near the proximal end of the lead means, and the second electrode which is electrically isolated from the first electrode is electrically connected to a second terminal means also near the proximal end of the lead means. The invention further includes a pacemaker means which includes a first pulse output means for generating atrial stimulation pulses, a first connector means electrically connected to the first pulse output means and adapted to engagingly receive the first terminal means, a P-wave sensing EGM amplifier means for sensing P-waves generated by spontaneous and stimulated atrial action, a second connector means electrically connected to the input of the P-wave sensing EGM amplifier means and adapted to engagingly receive the second terminal means, and a means for monitoring the output of the P-wave sensing EGM amplifier means in the presence of atrial stimulation pulses generated by the pulse output means for the purpose of determining if P-wave capture due to the atrial stimulation pulses has occurred.

In a specific embodiment of the invention, the first lead means is a conventional bipolar (two wires) atrial pacing lead having a distal electrode at its tip, and a ring electrode spaced apart from the tip, each electrode being electrically isolated from the other and connected to respective terminals at the proximal end of the lead. The ring electrode is connected to the input of a P-wave sensing EGM amplifier having bandpass characteristics such that the signals which normally appear on an atrial EGM in the presence of atrial stimulation pulses can be detected. The distal electrode at the tip is connected to a P-wave sense/pace amplifier and to an atrial pulse output circuit, the P-wave sense/pace amplifier being chosen to have a bandpass characteristic that allows positive detection of P-waves in the absence of stimulation pulses while discriminating against other non-P-wave signals present in the atrium. A unipolar (single wire) ventricular lead is also provided, this lead being connected to an R-wave sense/pace amplifier within the pacemaker as well as to a ventricular pulse output circuit. The outputs of the P-wave sensing amplifier, P-wave sense/pace amplifier, and R-wave sense/pace amplifier are provided to a switch controllable through a telemetry subsystem for selecting which of the amplifier outputs will be telemetered in real time to a remotely located monitor for physician analysis. Other embodiments of the invention provide for automatic setting of stimulation pulse amplitudes in response to a determination of P-wave capture thresholds.

It is obvious that the stimulating electrode need not be at the tip or that the second electrode be a ring. Basically, they must simply be adapted to be spaced apart in the heart. The structures mentioned, however, are preferred.

In operation, the ring electrode being spaced apart from the stimulation electrode does not receive the high energy output present at the stimulation electrode during atrial stimulation. This is because of attenuation within the heart itself and because the ring electrode is not connected to the output circuit. Thus, the bandpass characteristics of the P-wave sensing amplifier are chosen so that a P-wave as well as other electrical signals within the atrium can be detected immediately after an atrial stimulation pulse. By telemetering the output of the P-wave sensing amplifier to a monitor for analysis by a physician, the physician can determine if P-wave capture has occurred by looking at the time differential between the atrial stimulation pulse and the occurrence of a P-wave. If this time differential remains constant, and if it is of a proper duration as determined by the spaced-apart distance between the first and second electrodes, the physician may conclude that P-waves are being generated as a result of the atrial stimulation pulses rather than spontaneous, or native, atrial activity. If on the other hand, the time differential between the occurrence of the stimulation pulse and the P-wave varies from cycle to cycle, then the physician can assume that capture has not occurred and that the P-waves appearing on the trace are being generated by spontaneous atrial activity. In this event, the physician can increase the amplitude or the pulse width of the stimulation pulses until such time as the stimulation pulse/P-wave occurrence time interval is constant between successive cycles, thereby indicating that the stimulation pulses are causing P-wave generation. It is possible, although unlikely, that spontaneous P-wave generation is present at a frequency equal to that of the atrial stimulation pulses. However, because the distance from the distal electrode in the atrium to the ring electrode is known, and the distance from the ring electrode to the heart sinus node can be estimated, and the propagational characteristics of atrial stimulation events within the heart are known, the physician can also measure the time differential between occurrence of the atrial stimulation pulse and the P-wave and determine if this time differential corresponds to the distance between the distal electrode and the ring electrode or to the distance between the sinus node and the ring electrode This provides one manner in which the physician can determine if P-wave capture has occurred due to atrial stimulation pulses.

In some implantations, the ring electrode may be at or near the sinus node. Atrial capture can still be determined in accordance with the invention.

In a further embodiment of the invention, a pacemaker is disclosed which has the capability to automatically adjust the amplitude of the atrial stimulation pulses until a sufficient amplitude is maintained to effect atrial P-wave capture.

BEST MODE FOR CARRYING OUT THE INVENTION

Detailed illustrative embodiments of the invention disclosed herein exemplify the invention and are currently considered to be the preferred embodiments for such purposes. They are provided by way of illustration and not limitation of the invention. Various modifications thereof will occur to those skilled in the art, and such modifications are within the scope of the claims which define the present invention.

In the preferred embodiment, a heart pacing system is disclosed in which a conventional bipolar atrial lead is utilized in conjunction with an implantable pacemaker having one P-wave sense/pace amplifier attached to an atrial stimulation electrode at the lead distal end, or tip, and another P-wave amplifier attached to a spaced-apart ring electrode near the distal end of the lead. The P-wave sense/pace amplifier electrically connected to the stimulation electrode has bandpass characteristics which allow a P-wave to be detected in the absence of a stimulation pulse and discriminate against non-P-wave signals present in the atrium. The output of the P-wave sense/pace amplifier is used to inhibit atrial stimulation pulse generation in the presence of a naturally-occurring P-wave. The other P-wave amplifier attached to the ring electrode has bandpass characteristics chosen to detect both naturally occurring P-waves and P-waves in response to stimulation pulses for the purpose of determining if P-wave capture has occurred. Whenever the time periods between stimulating pulses and the next-occuring P-waves are substantially constant, the physician can be generally assured that P-wave capture has occurred. The amplitude of the stimulation pulse can then be lowered to such a value that P-wave capture can be maintained with the least possible power drain from the pacemaker battery. The pacemaker disclosed is typically of the DDD type in which pacing and sensing in both the atrium and ventricular chambers of the heart are possible. Accordingly, a second ventricle lead and an associated R-wave sense/pace amplifier within the pacemaker are also provided. A switch responsive to signals received through the pacemaker telemetry system is also provided so that the output of either P-wave amplifier, or the R-wave amplifier can be transmitted in real time to an external monitor for analysis by a physician. It should be recognized however that the invention is not limited to a DDD type pacemaker and other pacemaker types could be utilized such as AAI and AAT pacemakers for example.

Figure 1:
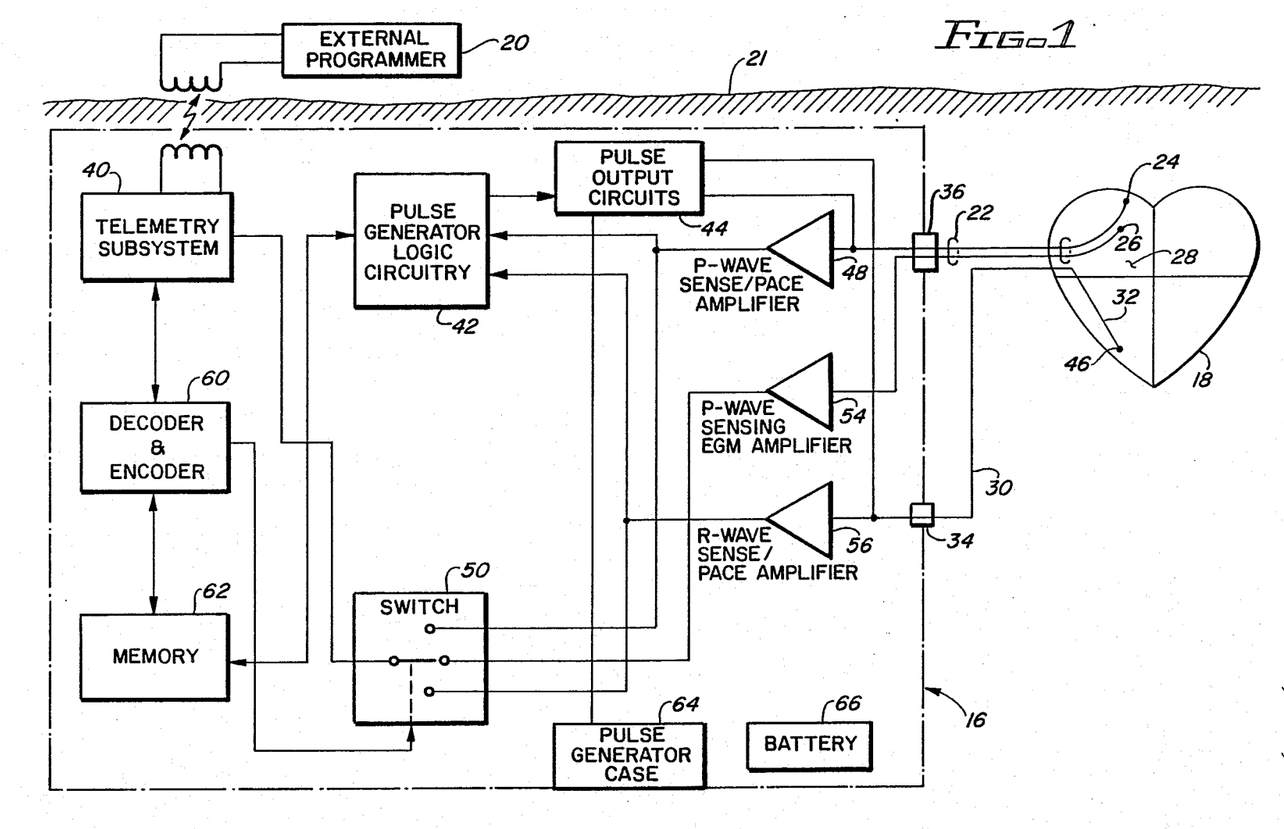
FIG. 1 is a block diagram of a pacemaker according to the present invention.

Referring now to FIG. 1, a block diagram of an implanted pacemaker 16 according to the invention is shown, the pacemaker 16 being connected to a user's heart 18 and electromagnetically in, contact with an external programmer 20, which programmer 20 includes a telemetry transmitter and receiver and monitor external to the user's skin 21. A conventional bipolar atrial lead 22 is provided having a first or tip electrode 24 at its distal end and a second electrode 26 spaced apart from the tip electrode 24 and in the configuration of a typical bipolar lead ring electrode. It may be understood that a second ring electrode and an associated amplifier may be used for greater signal strength in sensing the electrical activity in the atrium. The tip electrode 24 is located in contact with atrial tissue of the heart atrium 28. A unipolar ventricle lead 30 is located in the heart ventricle 32 and is attached to the pacemaker 16 through a ventricular connector 34. The atrial lead 22 is connected to the pacemaker 16 through an atrial connector 36. The pacemaker 16 includes a telemetry subsystem 40 for transmitting data and parameter values to the external telemetry transmitter and receiver of the external programmer 20, and for receiving data instructions and the like from the external programmer 20. The pacemaker 16 also includes pulse generator logic circuitry 42 which, in turn, controls pulse output circuits 44 for providing both atrial and ventricle stimulation pulses. The atrial output of the pulse output circuits 44 is connected through the atrial connector 36 to the atrial tip electrode 24 for stimulation of the atrium; the ventricle output of the pulse output circuits 44 is connected through the ventricle connector 34 to a ventricle tip electrode 46 for stimulation of the ventricle. A P-wave sense/pace amplifier 48 having bandpass characteristics as explained below is also connected through the atrial connector 36 to the atrial tip electrode 24 for receiving electrical signals present at the electrode 24. The output of the P-wave sense/pace amplifier 48 is also connected to the pulse generator logic circuitry 42 and to an ECG switch 50, the purpose of which will be explained below. The implanted pacemaker, in operating as a "demand" type pacer, would not provide stimulation to the atrium when amplifier 48 provided its output indicating an intrinsic P-wave. A second amplifier, a P-wave sensing EGM amplifier 54 having bandpass characteristics as explained below has its input connected through the atrial connector 36 to the second atrial electrode 26. The output of the P-wave sensing amplifier is also connected to the switch 50. An R-wave sense/pace amplifier 56 is also provided, its input being connected to the pulse output circuits 44 and the ventricle tip electrode 46 through the ventricle connector 34. The output of the R-wave sense/pace amplifier 56 is connected to the pulse generator logic circuitry 42 for inhibiting a ventricle stimulation pulse in the presence of spontaneous ventricular activity, and to the switch 50. Amplifier 56 has a sufficiently broad band-pass to pass electrical signals of substantially all native (intrinsic) ventricular activity. The output of the switch 50 is connected via a line 58 to the telemetry subsystem 40 for real time transmission of the output of either the P-wave sense/pace amplifier 48, the P-wave sensing amplifier 54 or the R-wave sense/pace amplifier 56. The specific amplifier output to be transmitted is selected by the physician via instructions transmitted by the external telemetry transmitter and receiver 20 and received by the implanted telemetry subsystem 40. These instructions are decoded by a decoder and encoder 60. The output of the decoder and encoder 60 is utilized to establish which amplifier output 48, 54 or 56 is to be connected to the telemetry system 40 for transmission to the external telemetry transmitter and receiver 20. Although the switch 50 is shown as a switch, it should be readily apparent that any kind of selectable connecting means could be employed to provide continuity between one of the amplifiers 48, 54 and 56 and the line 58. Further, two or more of the amplifier outputs could be transmitted simultaneously if proper provisions were made within the telemetry subsystem 20. In addition, a memory 62 is provided which receives parameter information from the decoder and encoder 60, this parameter information being utilized to control the pulse generator logic circuitry 42. The tip electrode 24 for stimulating the atrium and the tip electrode 46 for stimulating the ventricle are all utilized in a unipolar configuration with the return path being provided through a conductive portion of the pulse generator case 64 which is connected to the pulse output circuits 44. A battery 66 is also incorporated for providing power to the implanted pacemaker 16. It should also be recognized that although an implanted pacemaker is shown for illustrative purposes, the invention is in no way limited to an implanted pacemaker. An external pacemaker could also be provided in accordance with the teachings of the invention. Further, although a unipolar ventricular lead was chosen for illustrative purposes, a bipolar ventricular lead could also have been utilized provided appropriate connectors were available on the pacemaker. Similarly, a multi-conductor atrial lead could be provided with two of the conductors providing a bipolar atrial lead and the third conductor being connected to the P-wave sensing ECG amplifier 54 shown in FIG. 1.

Figure 2:
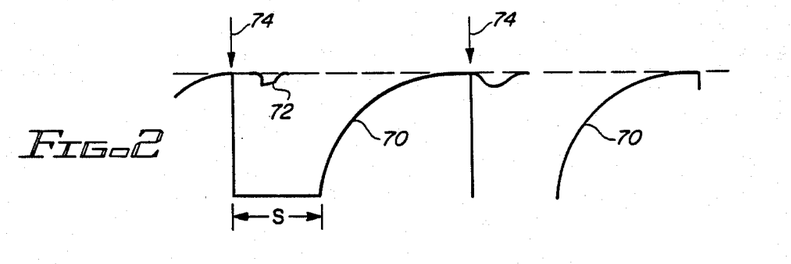
FIG. 2 is a waveform diagram illustrating the problem of P-wave detection utilizing the atrial stimulation electrode as a P-wave sensing electrode.

Operation of the implanted pacemaker 16 shown in FIG. 1 can be best understood by reference to FIGS. 2, 3, 4A and 4B. As previously explained, one of the problems associated with atrial pacing is determining whether P-wave capture has been effected by atrial stimulation pulses. In prior art systems, the sensing circuit corresponding to the P-wave sense/pace amplifier 48 in FIG. 1 sensed signals present at the electrode at the lead distal end which corresponds to the tip electrode 24 in FIG. 1. Referring now to FIG. 2, the voltage present at the output of the P-wave sense/pace amplifier 48 in the presence of an atrial stimulation pulse corresponds in general to the waveform shown at 70. Thus, the output of the P-wave sense/pace amplifier 48 is saturated during the period "S" shown in FIG. 2. Because the P-wave voltage is small with respect to the saturation voltage caused by the stimulation pulse as shown by the dotted line 72, it is difficult, if not impossible, to pick out the time at which the P-wave occurred relative to the stimulation pulses which occur at the times indicated by the arrows 74. Because of this difficulty in determining when the P-wave 72 actually occurred relative to stimulation pulse occurrence as shown at 74, it is difficult for the physician to determine if the stimulation pulse has effected P-wave capture.

Figure 3:
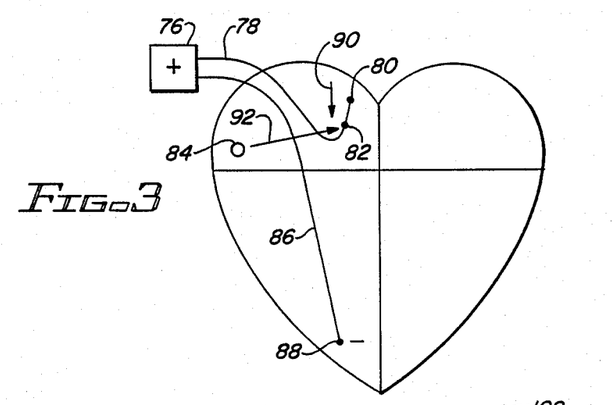
FIG. 3 is a schematic representation of a user's heart showing locations of the atrial and ventricle electrodes.

Referring now to FIG. 3, a representation of the heart is shown, showing a pacemaker 76 according to the invention, having a conventional atrial lead 78 and, also having a stimulation and sensing electrode 80 at its distal end and a second or P-wave sensing electrode 82 spaced apart from the stimulation electrode 80. By way of example only, the atrial lead 78 is configured in the form of a J at its distal end so that the stimulation electrode 80 can be located within the atrial appendage (not shown). The heart sinus node 84 is also shown, as well as a ventricle lead 86 having its stimulation electrode 88 located in the ventricular apex. It can be appreciated that the further the sensing electrode 82 is spaced-apart from the stimulation electrode 80, the less the stimulation pulses will interfere with P-wave sensing by the sensing electrode 82. This is because of an attenuation of the electrical stimulation signal due to intervening blood and heart tissue. However, it should be apparent that the sensing electrode 82 cannot be so far removed from the stimulation electrode 80 that it would no longer be within the heart atrium. All electrodes 80, 82 and 88 use the case of the pacemaker 76 as a return electrode, the case being positive with respect to a negative going pulse present at both stimulation electrodes 80 and 88. Another advantage of utilizing the spaced-apart sensing electrode 82 for P-wave detection is that the P-wave electrical characteristics as picked up by the sensing electrode 82 differ because of the direction of propagation as shown by the arrows 90 and 92, arrow 90 showing the propagation direction from the stimulation electrode 80 and arrow 92 being the propagation direction from the sinus node 84. This allows the physician to determine if the P-wave occurred as a result of spontaneous atrial activity or stimulated atrial activity. Further, because of the different distances between the sensing electrode 82, the sinus node 84 and the stimulation electrode 80, it can be appreciated that even if the sinus node 84 is operating in synchronism with the stimulation pulses, the known propagation time between a stimulation pulse and P-wave generation could be used to determine if P-wave generation were due to spontaneous or stimulated atrial activity. Further, it can be appreciated that although a typical bipolar atrial electrode 78 is utilized, all three electrodes 80, 82 and 88 operate in a unipolar manner in that they all use the pacemaker 76 case as a common return electrode.

Figure 4A:
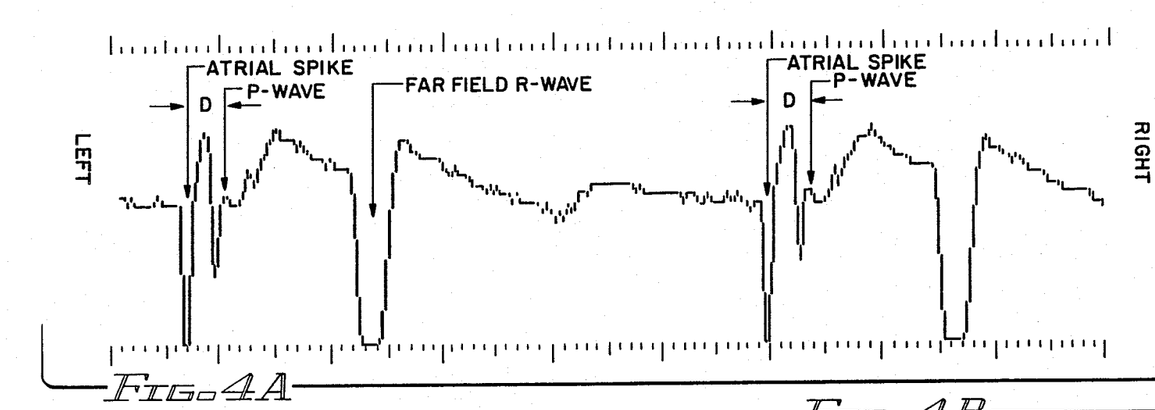
FIGS. 4A and 4B are waveform diagrams of intercardiac electrogram (EGM) signals, as viewed by a physician on programmer 20 of FIG. 1 FIG. 4A illustrating an EGM signal showing P-wave capture and FIG. 4B illustrating an EGM signal in the absence of P-wave capture.
Figure 4B:
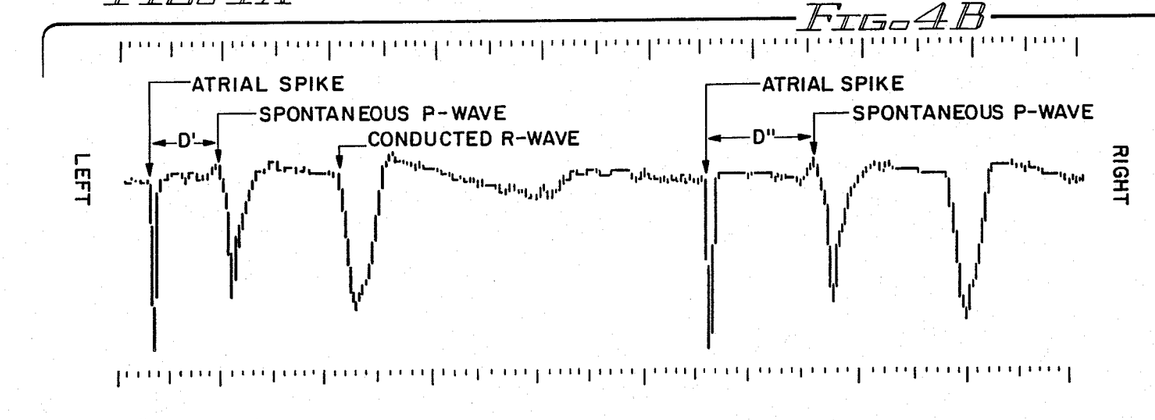

Detection of atrial capture can be further understood in reference to FIGS. 4A and 4B. Referring to FIG. 4A, atrial stimulation pulses 100 and ventricular stimulation pulses 102 can be seen. Further, P-waves 104 and R-waves 106 can also be seen. The time differential D between atrial stimulation and P-wave occurrence in successive cycles can be seen to be constant. Thus, the physician can assume that P-wave capture as a result of the atrial stimulation pulses has occurred provided that the distance D corresponds approximately to the propagation delay due to the distance between the stimulation electrode 80 and the sensing electrode 82 as explained in conjunction with FIG. 3. Referring now to FIG. 4B, the time differentials D' and D" between the atrial stimulation pulses and P-wave occurrences can be seen to be different. Thus, the physician can conclude that P-wave capture by the atrial stimulation signals has not occurred but that the P-waves are spontaneous or "native" or "intrinsic" in origin. Under normal circumstances with respect to FIG. 4B, the physician would assume that the magnitude of the stimulation pulses is below the stimulation threshold of the particular patient's atrium and would accordingly increase their magnitude until P-wave capture occurred, that is, until an EGM signal similar to that shown in FIG. 4A is observed on the monitor of the external programmer 20. Again, in prior art systems, it would be impossible to observe the presence of P-waves utilizing the stimulation electrode 80 as the sensing electrode due to saturation of the P-wave sense/pace amplifier caused by the atrial stimulation pulse.

Figure 5:
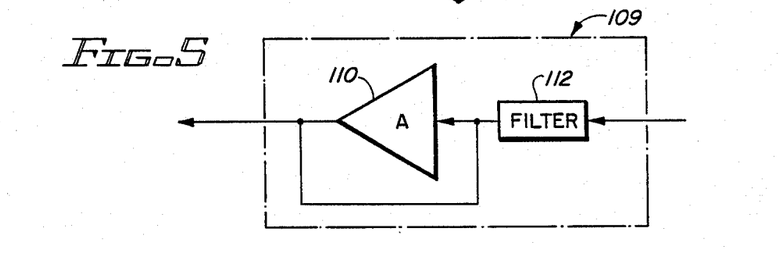
FIG. 5 is a block diagram of a P-wave amplifier shown in FIG. 1.

FIG. 5 shows a simplified block diagram of a typical P-wave or R-wave wave amplifier 109 such as those shown in FIG. 1 as blocks 48, 54 or 56. The amplifier 109 includes an amplification portion 110 and an input filter 112. The difference between the P-wave sense/pace amplifier 48 and the P-wave sensing amplifier 54 is in the bandpass characteristics of the amplification portion 110 and filter 112 combination. The amplitude and bandpass characteristics of the P-wave sense/pace amplifier 48 are chosen to provide to the pulse generator logic circuitry 42 a positive indication of P-wave occurrence in the absence of an atrial stimulation pulse, while at the same time rejecting non-P-wave signals such as far-field R-wave signals and muscle electrical noise. This is to allow the pulse generator logic circuitry 42 to determine if the atrium is operating spontaneously or whether an atrial stimulation pulse is required. The purpose of the P-wave sensing amplifier 54 is to provide an electrogram of all, or most all, atrial electrical action including an indication of P-wave occurrence in the presence of an atrial stimulation pulse. Thus, the precise characteristics of the P-wave and its location with respect to an atrial stimulation pulse must be analyzed to determine if the P-wave is occurring spontaneously or is occurring as a result of an atrial stimulation pulse. In order to meet these different requirements, the amplification portion 110 filter 112 combination of the P-wave sense/pace amplifier 48 as shown in FIG. 1 can be chosen to have a center frequency at 60 Hz and 3 db points at approximately 10 Hz and 100 Hz. The purpose of this U-shaped frequency response is to maximize detection of the P-wave which has a large frequency component near 60 Hz and to reject other signals such as some of that from the heart R-wave which by the time it reaches the atrium has lower frequency components and muscle electrical noise which has higher frequency components. Thus, the bandpass characteristics of the P-wave sense/pace amplifier must be chosen to attenuate all electrical signals within the atrium other than the one frequency that most characterizes the P-wave. Of course the bandpass characteristics described above are only representative of one embodiment, and other U-shaped response characteristics could be chosen. For example, the peak of the response curve could be chosen to lie between 40 Hz and 80 Hz and the 3 db points could lie between 0.1 Hz and 500 Hz. The teaching of the invention merely is that the P-wave sense/pace amplifier be chosen to pass signals characteristic of the P-wave while tending to reject signals that are not characteristic of the P-wave. Thus peak detection circuitry in the pulse generator logic circuitry 154 can be triggered by the output of the P-wave pace/sense amplifier 44 without danger of a false detection due to other electrical activity in the atrium.

The P-wave sensing EGM amplifier 54 is chosen to have a response that is essentially flat between $3\frac{1}{2}$ Hz and 125 Hz. This is to allow the physician to see all electrical atrial activity for a complete understanding of the atrial electrical environment including any T-wave ventricle signals and any far-field R-wave signals that are present. However, the invention is in no way limited to a P-wave sensing EGM amplifier having a flat response, and a U-shaped frequency response such as that of the P-wave sense/pace amplifier could also be utilized. However, use of such a U-shaped frequency response would limit the EGM information available to the physician without any compensating advantage.

Figures 6, 9:
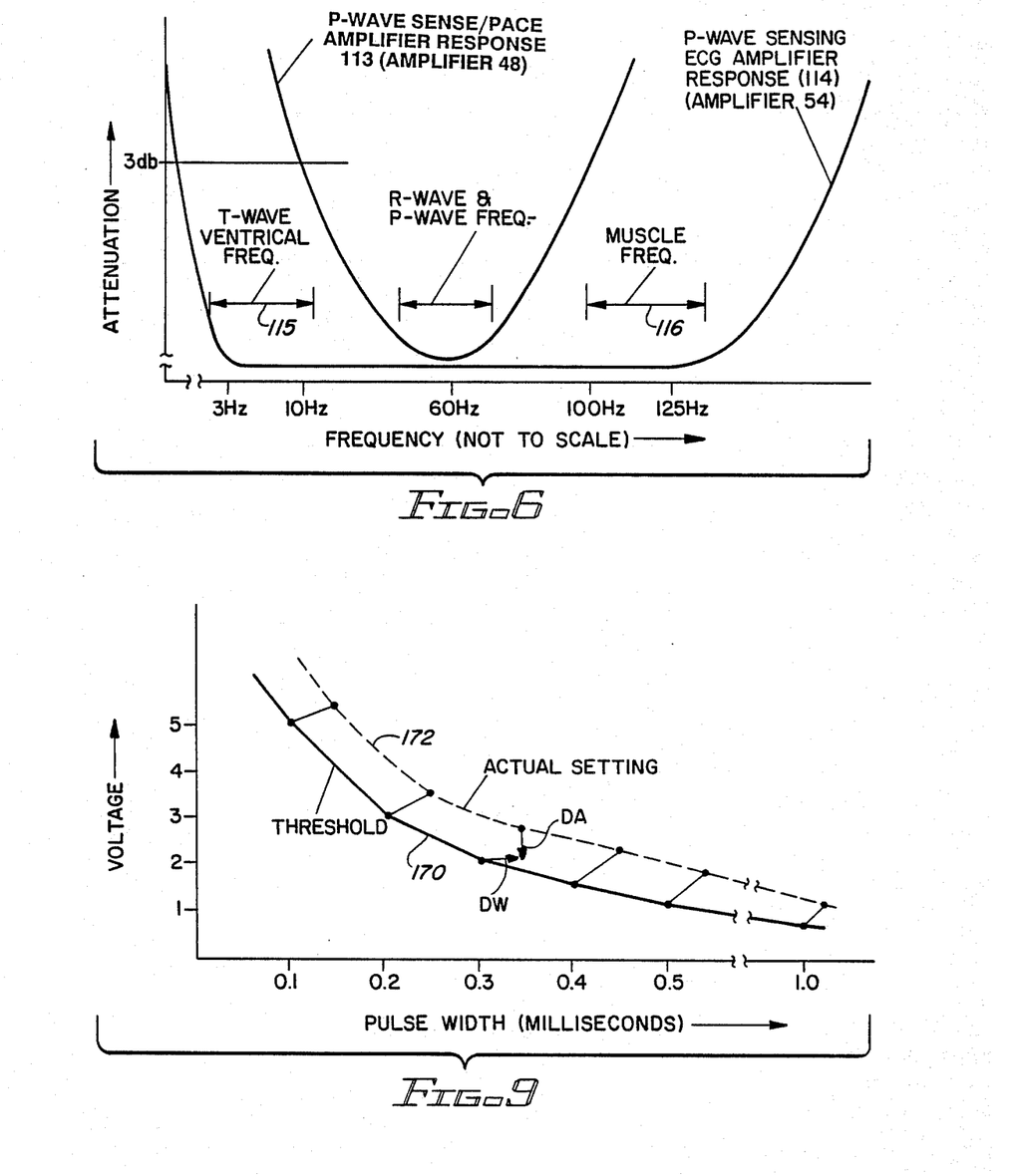
FIG. 6 shows frequency response curves for the P-wave sense/pace amplifier and the P-wave sensing amplifier.
FIG. 9 illustrates a pulse voltage/pulse width curve showing P-wave capture as a function of pulse amplitude and pulse width.

The above can be further understood by referring to FIG. 6. Here the P-wave sense/pace amplifier response 113 and the p-wave sensing EGM amplifier response 114 can be seen. As can be seen, the response 113 is chosen to pass the p-wave frequency and attenuate the frequencies associated with other physiologic events as shown at 115 and 116 in order to provide a relatively high amplitude output corresponding only to R- and P-wave events. The response 114 is chosen to pass all frequencies in order to provide an accurate overall EGM signal to the physician. As shown, response 114, of the sensing amplifier includes T-wave ventricular frequencies and far-field signal.

Figure 7:
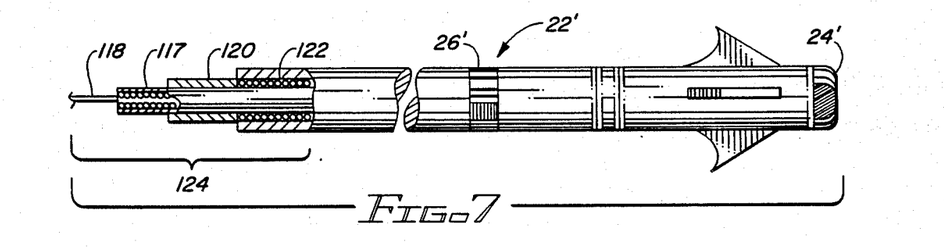
FIG. 7 is a partially cut-away atrial electrode utilized in the embodiment of FIG. 1.

Referring now to FIG. 7, a lead 22' of the type shown in FIG. 1 as 22 is illustrated. Although a straight shank lead is shown for illustrative purposes, it should be recognized that a typical atrial-J lead could be utilized in the application shown in FIG. 1, and thus a portion of the distal end of the lead could be J-shaped. The lead 22'. includes a tip electrode 24' which is connected through a spirally-wound conductor 117 to a first terminal 118. A ring electrode 26' is attached through a spirally-wound conductor 122 to a second terminal 120, this conductor 122 being electrically isolated from the conductor 117 attached to the tip electrode 24'. The terminals 118 and 120 are adapted to connect to appropriate connectors in the pacemaker. Although the connector or terminal arrangement generally shown at 124 is a typical in-line type of connector, other connector arrangements could be utilized such as having each terminal coming out of the proximal end of the lead to form a Y-shaped connector. The ring electrode 26' is spaced apart from the tip electrode 24' a distance such that when the tip 24' is located in the atrial appendage, the ring electrode 26' will also be located within the atrium. As previously explained, FIG. 7 merely illustrates a typical bipolar atrial lead which is utilized in the FIG. 1 embodiment while having its tip electrode and ring electrode operate in a unipolar fashion. Thus, an implantable pacemaker configured according to that shown in FIG. 1 can be utilized with conventional bipolar atrial leads without requiring a special purpose lead to be utilized.

Figure 8:
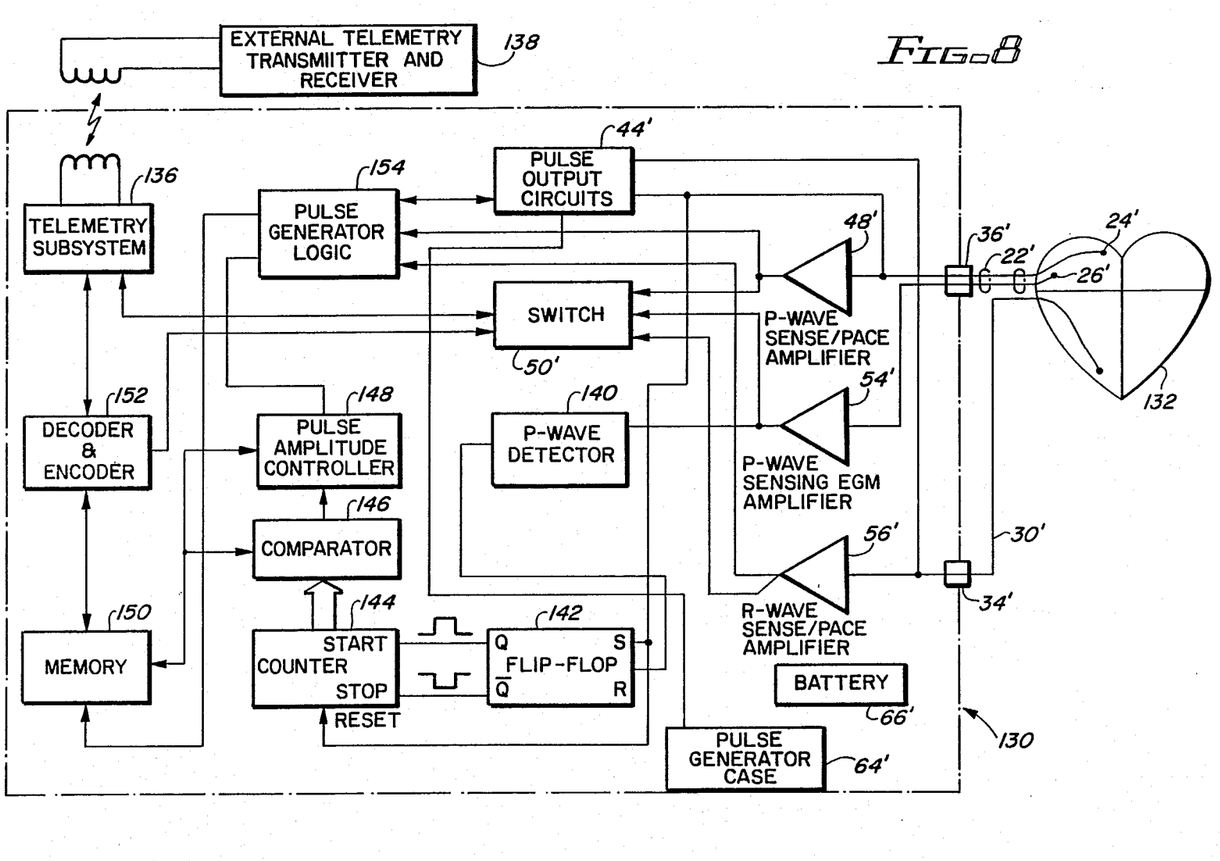
FIG. 8 is a block diagram of a further embodiment of the invention.

A further embodiment of the invention is shown in FIG. 8. This embodiment incorporates a means for automatically controlling the characteristics of the output atrial stimulation pulse in order to select an amplitude and/or width that would maintain P-wave capture without utilizing an unnecessarily large amplitude and/or width that would result in high battery current drains leading to premature battery depletion. Referring now to FIG. 8, an implantable pulse generator 130 is shown, the pulse generator 130 being connected through connectors 36' and 34' to the user's heart 132 through a conventional bipolar atrial-J lead 22' and a unipolar ventricle lead 30' in a manner identical to that as explained in conjunction with FIG. 1. Other components similar to those shown in FIG. 1 include the pulse output circuits 44', the switch 50', the P-wave sense/pace amplifier 48', the P-wave sensing amplifier 54', the R-wave sense/pace amplifier 56', the pulse generator case 64' and the ventricle lead connector 34'. The switch 50' operates in the same manner as the switch 50 shown in FIG. 1 in that the outputs of the P-wave sense/pace amplifier 48', the P-wave sensing amplifier 54' and R-wave sense/pace amplifier 56', are provided to the switch 50', which in turn is controlled by signals from other portions of the pacemaker to select which of the specific amplifier 48', 54' or 56' output signals will be transmitted in real time via a telemetry subsystem 136 to an external telemetry transmitter and receiver 138. The information from each of the amplifiers and, if desired, from the memory or other portion of the pacemaker may be displayed such as an electrocardiograph (ECG) 156. The output of the P-wave sensing amplifier 54', which is connected to the ring electrode 26' shown in FIG. 8 for the purpose of detecting P-waves in the presence of atrial stimulation pulses, is connected to a P-wave detector 140 for providing an output pulse synchronized with the occurrence of a sensed P-wave. The P-wave detector 140 includes conventional circuitry which produces a pulse output whenever the P-wave signal exceeds a predetermined level for a predetermined time. The P-wave detector also has an input bandpass characteristic similar to that of the P-wave sense/pace amplifier shown at 113 in FIG. 6 in order to attenuate other electrical signals in the atrium as explained above. The P-wave detector 140 output is connected to a reset terminal of a monostable flip-flop 142. A counter 144 is provided having a start terminal connected to the Q output of flip-flop 142 and a stop terminal connected to the $\bar{Q}$ output of flip-flop 142. The set input to flip-flop 142 and the reset input of the counter 144 are connected to the atrial stimulation output of the pulse output circuits 44'. The output of the counter 144 is connected to a comparator 146, the output of which is connected to a pulse amplitude, width controller 148. The comparator 146 and the pulse amplitude width controller 148 are further controlled by signals from a memory 150. Further, a decoder and encoder 152 is provided, the decoder and encoder 152 being connected to the telemetry subsystem 136 and the memory 150, and providing an output to the switch 50' for controlling which of the P-wave or R-wave amplifier outputs are to be transmitted in real time to the external transmitter and receiver 138 by the telemetry subsystem 136. The comparator 146 can be of any standard type well-known in the art, either digital or analog, that compares the elapsed time between the start and stop inputs to the counter 144 for determining time coincidence. If the elapsed times between the start and stop pulse inputs to the counter 144 are equal for successive stimulation pulse/P-wave intervals, then the pulse amplitude, width controller 148 is chosen to reduce the output voltage of the atrial stimulation pulse through the pulse generator logic circuitry 154 until such time as the output of the comparator 146 indicates that the elapsed time intervals between start and stop inputs to the counter 144 are, not equal. At that point, the pulse amplitude, width controller 148 increases the amplitude of the atrial stimulation pulses until the counts provided by the counter 144 are equal. As can be readily appreciated, this comparison can be effected digitally or can be effected by numerous analog circuits. A further refinement in the comparator 146, which again can be readily implemented by one familiar with electronic circuits, would be to reject start and stop elapsed times that correspond to the propagation time between the heart sinus node and the ring electrode 26' as compared with the propagation time between the distal electrode 24' and the ring electrode 26' as previously explained. Thus, if the atrium were functioning in synchronism with the atrial stimulation pulses, but P-wave capture had not been effected, this additional feature would prevent the system from operating as though P-wave capture had been achieved. Thus, one can readily appreciate that an implantable pacemaker has been disclosed in which through appropriate signals from the external transmitter and receiver 138, through the telemetry subsystem 136, the decoder and encoder 152 and the memory 150, the amplitude of the atrial stimulation pulses can be automatically lowered until P-wave capture is lost, and then slowly increased until P-wave capture is achieved, thus resulting in the most efficient use of battery power and maximization of the life of the implanted pacemaker. Further, the pacemaker through its memory 150 could be programmed to automatically effect this resetting of atrial stimulation pulse amplitude at predetermined time intervals such as every month without requiring the presence of an attending physician. Although not shown, it can be readily appreciated that such a system could also be utilized to set the output of the ventricular stimulation pulses. However, in the ventricle, the determination of R-wave capture is a less critical problem because of the magnitude of the R-wave with respect to the magnitude of the ventricle stimulation pulse.

In a still further embodiment of the invention, the memory 152 can be programmed using conventional techniques to set the atrial stimulation plus amplitude and pulse width optimally for conservation of battery power. Referring to FIGS. 8 and 9, the pulse generator logic 154 can be readily programmed through the memory 150 to set various pulse widths and determine the appropriate voltage thresholds for P-wave capture as explained in the discussion associated with FIG. 8. If, for example, threshold voltages for pulse widths in 0.1 millisecond increments between 0.1 milliseconds and 1.0 millisecond were taken, a P-wave threshold voltage versus pulse width curve as shown at 170 in FIG. 9 can be derived. For each pulse width increment reading, the current drain for the threshold stimulation pulse is measured and the power consumed computed by the pulse generation logic circuitry. The current measurement can be accomplished by several conventional methods all of which are well known in the art. From the known current utilized, and the voltage of the stimulation pulse, the power can be readily computed The power for each threshold measured is stored in the memory 150 and the pulse amplitude/pulse width combination providing the lowest power drain chosen Upon determining the pulse amplitude/pulse width combination that provides the lowest power drain, which may for example be 0.3 milliseconds at 2 volts as shown in FIG. 9, a delta pulse width DW and a delta pulse amplitude DA is programmed to be added to provide a margin of safety, or margin of operability. This margin of safety when applied to all the measurement points provides an "actual setting" curve shown at 172 in FIG. 9. The memory can be programmed to initiate this sequence at appropriate intervals, for example at one month intervals, to periodically ensure that the optimum pulse amplitude/pulse width combination is maintained.

Thus, a system has been disclosed whereby either the physician or the implanted pacemaker itself can determine if P-wave capture by atrial stimulation pulses has been effected, a capability that heretofore has been unachievable with conventional pacing systems.

What is claimed is:

1. A system for determining atrial capture comprising:
   heart pacing means for generating stimulation pulses;
   electrically conductive lead means for sending electrical stimulation pulses to and receiving electrical signals from a desired atrial location, said lead means including
   a first electrically conductive electrode connected to said heart pacing means, and
   a second electrically conductive electrode spaced apart from said first electrode;
   an amplifier connected to receive signals sensed by said second electrically conductive electrode, said amplifier including receiving means for receiving signals indicative of any atrial P-wave sensed by said second electrode, whether said atrial P-wave is a naturally occurring P-wave or a P-wave resulting from the application of a stimulation pulse applied to said first electrode, said amplifier further having means for generating an output signal indicative of the sensing of said atrial P-wave; and
   means responsive to the presence of said output signal for determining whether atrial capture has occurred, said means for determining atrial capture comprising means for measuring successive time intervals between application of an atrial stimulation pulse through said first electrode and the generation of the output signal by said amplifier, atrial capture being indicative if said measured time interval remains constant and corresponds approximately to a predetermined time interval.

2. The system recited in claim 1 wherein said first and second electrodes are spaced apart at least one-half inch.

3. The system recited in claim 1 wherein the amplifier includes means for amplifying frequencies within the range of 3 to 125 Hz.

4. The system recited in claim 1 wherein said lead means further includes a third electrode electrically coupled to said heart pacing means through which stimulating pulses can be provided for stimulating the ventricle, and a second amplifier coupled to said third electrode that senses R-wave signals originating in the ventricle, said second amplifier generating a second output signal indicative of the sensing of an R-wave at said second amplifier, said second output signal being provided to said heart pacing means to signal that an R-wave has occurred.

5. The system recited in claim 1 wherein there is further included:
   means for controlling the magnitude of the atrial stimulation pulses of said heart pacing means including means for reducing the magnitude of said atrial stimulation pulses until said atrial capture-determining means indicates lack of capture, and then increasing the magnitude of said stimulation pulses until said atrial capture-determining means indicates capture.

6. The system of claim 1 wherein there is further included means for controlling the magnitude of the atrill stimulation pulses generated by said heart pacing means in response to said atrial capture determining means.

7. A system for determining capture in response to pacemaker supplied electrical stimuli provided to a heart comprising:

a lead having proximal and distal ends, said lead having a first exposed electrically conductive electrode at said distal end, a second exposed electrically conductive electrode near said distal end, spaced apart and electrically isolated from said first electrode, first and second terminals near the proximal end of said of said lead, and first and second conductor means for electrically connecting said first and second electrodes, respectively, to said first and second terminals; and pacemaker means comprising pulse output means for generating stimulation pulses and applying said pulses to the first terminal of said lead, whereby said stimulation pulses are delivered to said first electrode of said lead, a sensing amplifier connected to said second terminal of said lead, said sensing amplifier generating an output signal in response to sensed electrical signals applied thereto through said second terminal, said electrical signals being generated by spontaneous and stimulated cardiac activity, and means for determining capture, said means for determining capture including means for monitoring the output signal of said sensing amplifier, said monitoring means including means for measuring successive time intervals between application of a stimulation pulse through said first electrode and the generation of the output signal by said sensing amplifier, said capture means providing an indication of capture if said measured time interval remains constant and corresponds approximately to a predetermined time interval.

8. A cardiac pacing system comprising:

lead means for providing electrical contact with a desired cardiac location, said lead means having first and second terminals at the lead proximal end, a first electrode at the lead distal end being electrically connected to said first terminal, a second electrode near the lead distla end being spaced apart and electrically insulated from said first electrode and being electrically connected to said second terminal; and pacemaker means comprising first connector means for electrically engaging said first terminal, second connector means for electrically engaging said second terminal, pulse generating means connected to said first connector means for providing a stimulation pulse, sensing EGM amplifier means connected to said second connector means for sensing electrical signals representative of cardiac action and for generating an output signal in response thereto, capture-determining means for determining if the stimulation pulse generated by said pulse generation means has produced capture, said capture-determining means including means for measuring the time interval between application of a stimulation pulse by said pulse generation means and the occurrence of the output signal from said sensing EGM amplifier means, capture being indicated if said measured time interval remains constant and corresponds approximately to a predetermined time interval, and adjustment means coupled to said pulse generating means for increasing the energy of subsequent stimulation pulses in the event said capture-determining means indicates capture has not occured.

9. A method of determining capture of stimulation pulses comprising the steps of:

(a) generating a stimulation pulse and applying it to a prescribed location to be stimulated;

(b) sensing electrical activity at a location spaced apart from the stimulating location of step (a);

(c) measuring the time delay between the application of the stimulation pulse of step (a) and the sensing of electrical activity of step (b); and (d) adjusting the magnitude of the stimulation pulses until the time delay measured in step (c) for successive measurements is substantially the same and within a prescribed tolerance of an expected propagation time delay, denoting captured stimulation pulses.

10. The method of determining capture of claim 9 wherein step (c) of adjusting the magnitude of the stimulation pulses comprises adjusting the stimulation pulse width.

11. The method determining capture of claim 9 wherein step (c) of adjusting the magnitude of the stimulation pulses comprises adjusting the stimulation pulse amplitude.

12. The method of determining capture of claim 9 wherein step (c) of adjusting the magnitude of the stimulation pulses comprises decreasing the stimulation pulse magnitude until the time delay measured in step (b) for successive measurements is not substantially the same, indicating lack of capture, and increasing the stimulation pulse magnitude in prescribed increments until the time delay measured in step (b) for successive measurements is substantially the same and within said prescribed tolerance of an expected propagation time delay, indicating captured stimulation pulses.

* * * * *